United States Patent [19]

Takaoka et al.

[11] Patent Number: 5,099,053

[45] Date of Patent: Mar. 24, 1992

[54] FLUORINE-CONTAINING ORGANIC SILICON COMPOUNDS AND A MANUFACTURING METHOD THEREOF

[75] Inventors: Akio Takaoka, Kanagawa; Noriyuki Koike, Yoshii; Hideki Fujii, Annaka, all of Japan

[73] Assignee: Shin-Etsu Chemical Co., Ltd., Tokyo, Japan

[21] Appl. No.: 528,425

[22] Filed: May 25, 1990

[30] Foreign Application Priority Data

May 26, 1989 [JP] Japan .................................. 1-133579

[51] Int. Cl.$^5$ .............................. C07F 7/08; C07F 7/18
[52] U.S. Cl. ..................................................... 556/448
[58] Field of Search ............................................. 556/448

[56] References Cited

U.S. PATENT DOCUMENTS

| | | | |
|---|---|---|---|
| 3,012,006 | 12/1961 | Holbrook et al. | 556/448 X |
| 3,334,123 | 8/1967 | Culpepper | 556/448 |
| 3,422,131 | 1/1969 | Pittman et al. | 556/448 |
| 3,772,346 | 11/1973 | Hess | 556/448 X |
| 4,898,958 | 2/1990 | Kishita et al. | 556/448 |

*Primary Examiner*—Paul F. Shaver
*Attorney, Agent, or Firm*—Oblon, Spivak, McClelland, Maier & Neustadt

[57] ABSTRACT

Fluorine-containing organic silicon compounds represented by the following general formula:

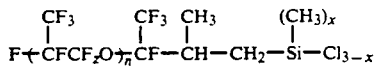

wherein n is any integer of 1 to 4, and x is any integer or 0 to 3; and a method of manufacturing the same compounds consisting of hydrosilylization between a hexafluoropropeneoxide oligoether derivative having an isopropenyl group at one end represented by the following formula:

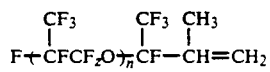

wherein n is any integer from 1 to 4, and a silane represented by the following formula:

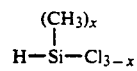

wherein x is any integer from 0 to 3.

1 Claim, 3 Drawing Sheets

FLUORINE-CONTAINING ORGANIC SILICON COMPOUNDS AND A MANUFACTURING METHOD THEREOF

BACKGROUND OF THE INVENTION

1. Field of the Invention

The present invention relates to novel fluorine-containing organic silicon compounds and a manufacture method thereof, the compounds being represented by the following general formula (1):

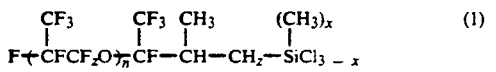

wherein n is an integer of 1 to 4, and x is an integer of 0 to 3. The compounds perform effectively as the following agents: silica treatment agents to be added to organic resins, silicone oil compounds, silicone rubbers, etc. for treatment of ≡Si—OH group existing in the silica surfaces of those substances; adhesive strength enhancing agents for materials such as a resist used in manufacturing processes of various semiconductor devices; and surface treatment agents for the surfaces of optical lenses, spectacle lenses, glasswares, etc. to impart thereto water and oil repellency and antifouling properties. Furthermore, the polysiloxanes obtained from the compounds have good low temperature properties and are highly heat resistant, water and oil repellent, and antifouling.

2. Background of the Prior Art

Various fluorine-containing organic silicon compounds have been known and used in the above-mentioned applications. However, due to the increased development of the technologies in the fields where these compounds are used, it is desired that such improved fluorine-containing organic silicon compounds be developed that have higher reactivities, and are capable of imparting to the materials greater chemical resistance, solvent resistance, heat resistance, weather resistance, water and oil repellency, and antifouling properties.

SUMMARY OF THE INVENTION

In order to develop such compounds, the inventors conducted earnest studies and eventually came to obtain novel fluorine-containing organic silicon compounds having the general formula (1) through the procedure described hereunder:

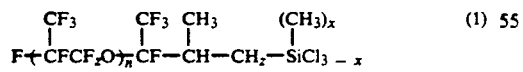

wherein n is an integer of 1 to 4, and x is an integer of 0 to 3.

These compounds can be made by the following pathway. First, hexafluoropropeneoxide (HFPO) is blown in an aprotic solvent-based solution of a metal fluoride to thereby synthesize an HFPO oligomer; to this is added methanol and then Grignard's reagent CH₃MgX whereby a novel hexafluoropropeneoxide oligoether derivative (3) having a dimethylcarbinol group at one end is obtained:

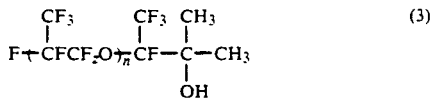

Thereafter, the derivative (3) is dehydrated to obtain a novel hexafluoropropeneoxide oligoether derivative having an isopropenyl group at one end of the molecule (2):

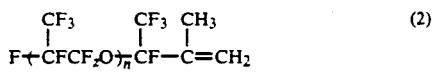

Finally, a silane having the following formula is put to react with the compound (2) whereupon the compound (1) is obtained.

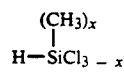

The new compound (1) exhibits the reactivity of chlorosilane and such properties ascribable to fluorocarbon, and thus can be useful as silica treatment agents to be added to organic resins, silicone oil compounds, silicone rubbers, etc. for treatment of ≡Si-OH group existing in the silica surfaces of those substances; adhesive strength enhancing agents for materials such as a resist used in manufacturing processes of various semiconductor devices; and surface treatment agents for the surfaces of optical lenses, spectacle lenses, glasswares, etc. to impart thereto water and oil repellency and antifouling properties. Furthermore, it was confirmed that the polysiloxanes obtained from those compounds have good low temperature properties and are heat resistant, water and oil repellent, and antifouling.

DETAILED DESCRIPTION OF THE FIGURES

Figure 1:
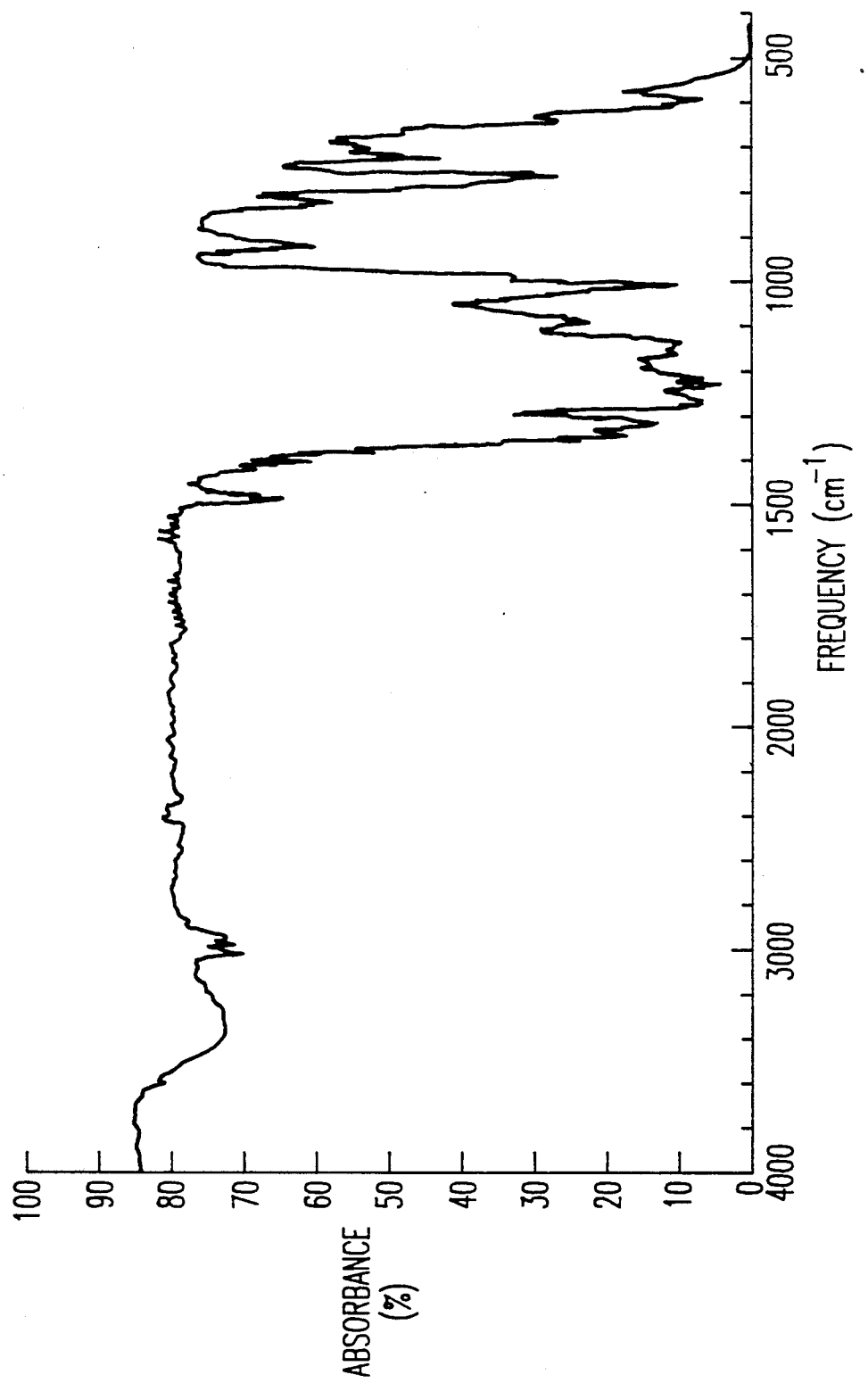
Figure 2:
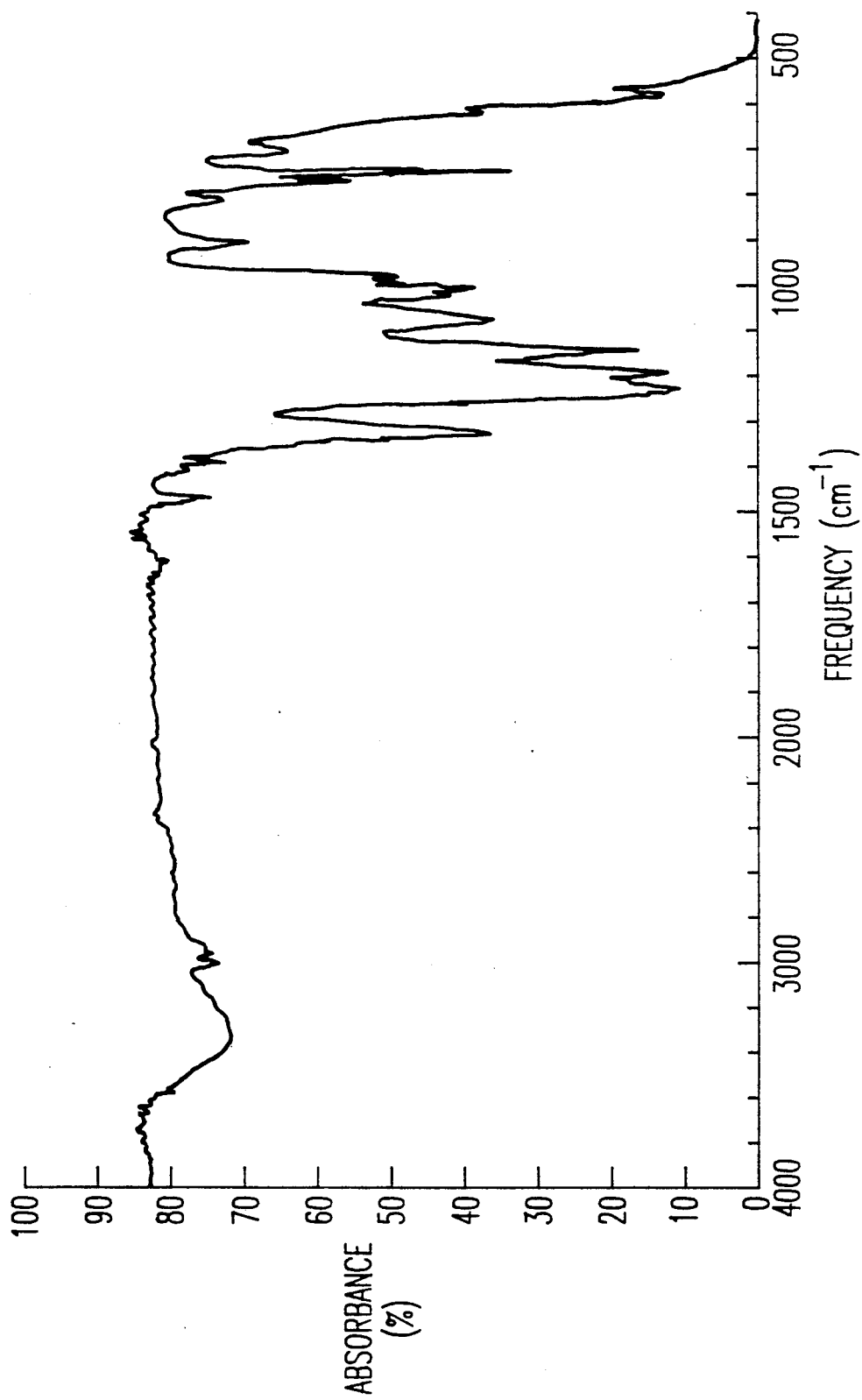
Figure 3:
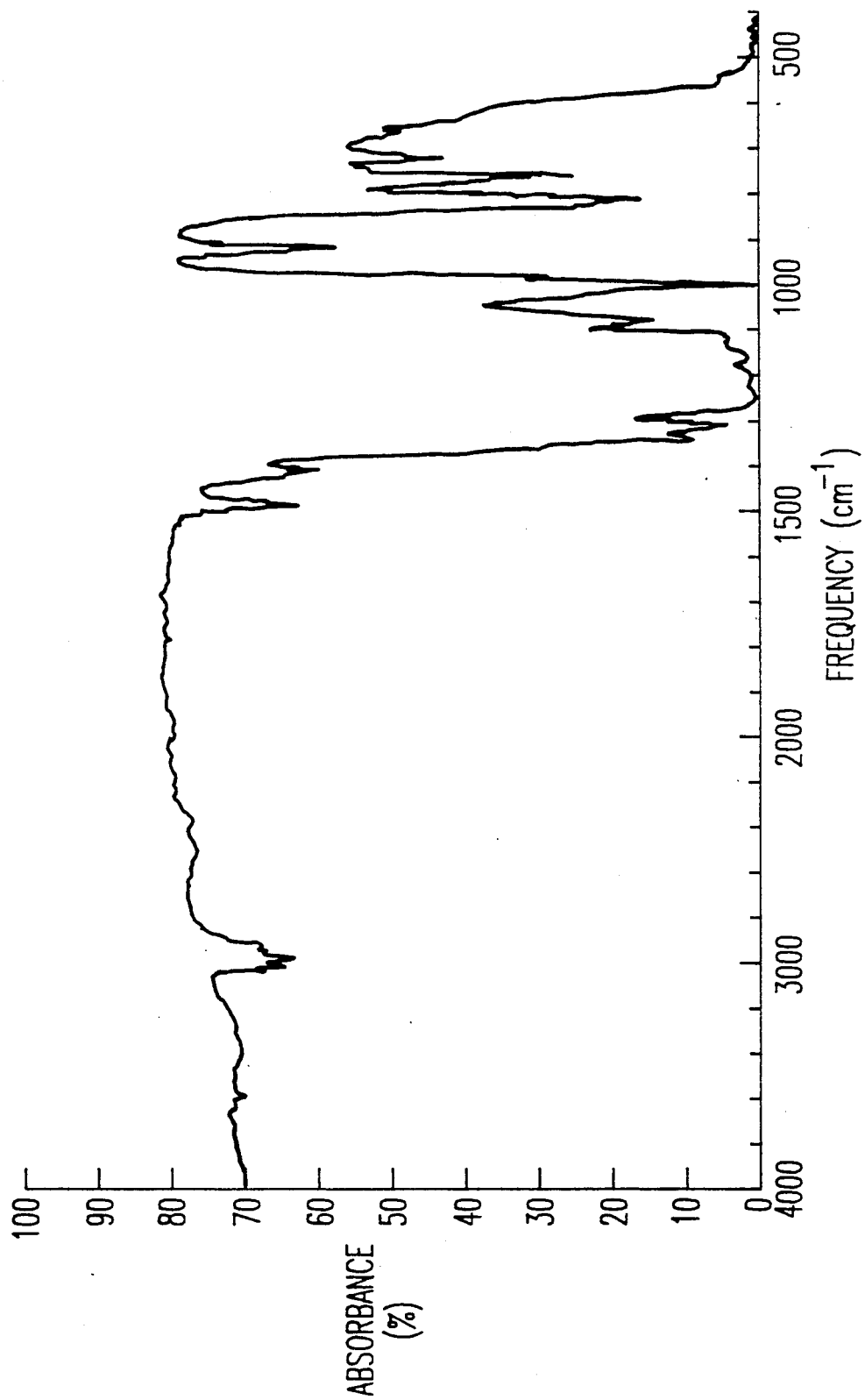

FIGS. 1-3 are IR spectra charts of 3 exemplary compounds of the invention.

DETAILED DESCRIPTION OF THE INVENTION

The synthetic scheme for the organic silicon compounds represented by the formula (1) is as follows:

① Oligomerization

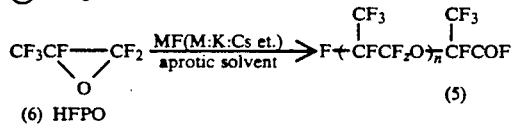

② Esterification

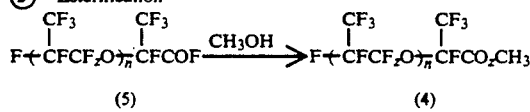

③ Carbinolization

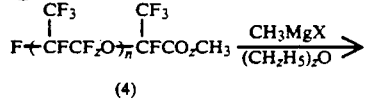

-continued

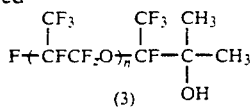
(3)

④ Dehydration

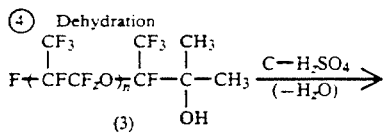

⑤ Hydrosilylation

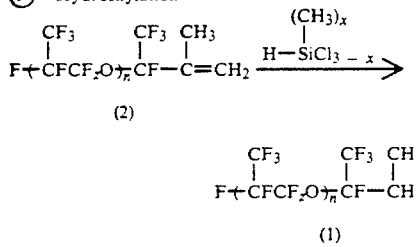

The oligomerization ① can be carried out through a known method. For example, by blowing the HFPO of formula (6) into an aprotic solvent-based solution of a metal fluoride at a low temperature, it is possible to obtain the HFPO oligomer acid fluoride represented by formula (5). The metal fluoride in the metal fluoride-aprotic solution can be potassium fluoride (KF), cesium fluoride (CsF), etc. The aprotic solvent can be diglyme, tetraglyme, tetrahydrofuran (THF), dimethylformamide (DMF), acetonitrile, etc. In the case of cesium fluoride (CsF)/tetraglyme system, the reaction condition under which the yield ratio of trimer becomes maximum is as follows:

| HFPO/CsF (molar ratio) | 103 |
| CsF/H$_2$O (molar ratio) | 2.83 |
| supply rate of HFPO | 1.57 g/min |
| reaction temperature | −5 to 0° C. |
| reaction time | 216 hours. |

Under this condition, the yield was 94%, and the oligomer yield ratio among the dimer, trimer and tetramer is 34%, 52% and 12%, roughly. The acid fluorides of these oligomers had boiling points differing from each other by about 50° C. so that it is easy to separate them by distillation.

The esterification ② is terminated immediately when this mixture of oligomer acid fluorides is dripped into an excessive amount of refrigerated methanol. Refinement and separation of the acid fluorides can be achieved by pouring a greatly excessive amount of water to it, and neutralizing, water-washing, and distilling the same.

After the oligomerization of the HFPO, it is possible to separate the respective oligomers of the esters (4) by pouring the oligomers into an excessive amount of alcohol, and esterifying and rectifying it after giving it the similar treatment as above.

Carbinolization ③ is effected by causing Grignard's reagent to react with the product, and a novel tertiary alcohol of formula (3) can be obtained.

In this case, the ester (4) is dissolved in a solvent such as ethyl ether, and this solution is dripped into a liquid which is prepared by adding methyl Grignard's reagent in a molar amount of 2 to 3 times as much as the ester of formula (4), preferably 2.1 to 2.5 times as much, to ethyl ether. The dripping should be continued till all of the ester is consumed in the reaction, and the reaction temperature should be maintained from 0° to 35° C., preferably from 20° to 30° C. If the reaction temperature is from 20° to 30° C., the reaction is completed within one hour.

The tertiary alcohol (3) is also obtained by causing the methyl Grignard's reagent to directly react with the acid fluoride (5).

The dehydration ④ is to dehydrate the tertiary alcohol (3), and as a result the compound represented by the formula (2) is synthesized. In this dehydration, 95% sulfuric acid in a molar amount of 3 to 20 times as much as the tertiary alcohol (3), preferably 4 to 7 times as much as the same, is used, and the dehydration is conducted at a temperature of 100 to 200° C., preferably 130° to 160° C., for several hours.

Next, the novel fluorine-containing organic silicon compound (1) of the present invention is synthesized by reacting a chlorosilane represented as

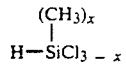

with the compound (2); this hydrosilylation proceeds favorably if chlorosilane is used in a molar amount of 1.1 to 1.5 times as much as the compound (2) and if the reaction is conducted in an autoclave in the presence of $1 \times 10^{-5} - 5 \times 10^{-3}$ mole of platinum catalyst at a temperature of 80° C. to 150° C. for 1 to 5 days.

The following reaction scheme has been known:

③' Carbinolization

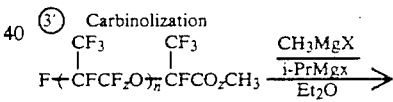
(b)

④' Dehydration

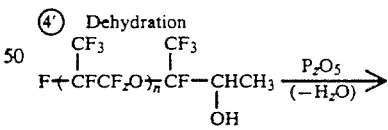

(a)

In this conventional method, the carbinolization ③' requires methyl- and isopropyl-mixed Grignard's reagent, and more than 1.5 times of the theoretically equivalent amount of isopropyl Grignard's reagent is needed as the reducing agent, and furthermore, it is necessary to carefully control the reaction temperature if it is desired that a particular product is selectively synthesized, and the reaction time is normally no less than 24 hours. What is more, in the dehydration ④', since the alcohol (b) is difficult to dehydrate, it is necessary to use diphosphorus pentaoxide and to keep the reaction temperature as high as 300° to 400° C. For the reasons stated so far, the above oligomer ethers are difficult materials to produce on the industrial scale, and the production costs are high.

In the case of obtaining the tertiary alcohol (3) from the ester (4) in accordance with the above method, as compared with the conventional method described above wherein the secondary alcohol (b) is produced, no isopropyl Grignard's reagent is required in the manufacturing process of the tertiary alcohol (3), and there is no need of carefully controlling the reaction temperature, and satisfactory results are obtained as the reaction proceeds at the room temperature. In contrast to the conventional method wherein the reaction to produce the secondary alcohol (b) takes more than twenty-four hours, in the inventive method the reaction to produce the alcohols takes only about an hour and the production selectivity of the tertiary alcohol (3) is very high so that it becomes easy to separate it and as a result it can be industrially manufactured advantageously and economically.

In addition to this, in the case of the inventive method, the dehydration of the tertiary alcohol (3), which proceeds as represented by the following reaction formula,

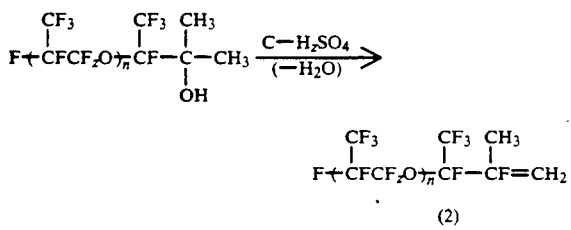

(2)

can be achieved easily and with a high yield at a temperature of about 150° C. and in the presence of inexpensive concentrated sulfuric acid, in contrast to the conventional method wherein the secondary alcohol (b) is dehydrated at a high temperature of 300° to 400° C. with the help of expensive diphosphorus pentaoxide, so that it is profitable to adopt the inventive method to manufacture on the industrial scale the novel oligoethers (2) of the HFPO having a isopropenyl group at one end.

Effects of the Invention

The thus obtained inventive fluorine-containing organic silicon compounds (1) have high reactivities due to the existence of the reactive chlorine atom(s) bonded to the silicon atom, and favorable properties ascribable to fluorocarbon, such as chemical resistance, solvent resistance, heat resistance, weather resistance, water and oil repellency, and antifouling properties due to the existence of terminal perfluoroalkyl ether group, which is represented as follows:

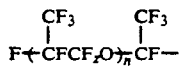

Consequently, the inventive fluorine-containing organic silicon compounds (1) can be used as silica treatment agents to be added to organic resins, silicone oil compounds, silicone rubbers, etc. for treatment of ≡Si—OH group existing in the silica surfaces of those substances; adhesive strength enhancing agents for materials such as a resist used in manufacture processes of various semiconductor devices; and surface treatment agent for the surfaces of optical lenses, spectacle lenses, glasswares, etc. to impart thereto water and oil repellency and antifouling properties. When used in the same manner in which existing conventional agents are used, the inventive compounds can impart to the treated materials properties such as chemical resistance, solvent resistance, heat resistance, weather resistance, water and oil repellency, and antifouling properties. The inventive compounds can be polymerized in conventional methods, and also can copolymerize with other silicon compounds to produce fluorine-containing organopolysiloxanes, which have good low temperature properties and are heat resistant, water and oil repellent, and antifouling.

The invention will be described in detail with reference to the examples, but the invention is not limited to the examples.

EXAMPLE 1

Magnesium (shaved to chips) in an amount of 36 g (or 1.5 mol) was placed in a dried 3-lit. four-neck flask, and to this was added dried ethyl ether in an amount of 200 ml. Then, an ethyl ether solution of methyl iodide ($CH_3I$) prepared by dissolving 230 g (1.5 mol) of methyl iodide in 300 ml of ethyl ether was dripped into the mixture by means of a dropping funnel at a rate sufficient to allow slow reflux, and this took about four hours.

Next, this flask was cooled in an ice bath, and after the cooling, an ethyl ether solution of ester prepared by dissolving 302 g of an ester (represented by the formula below; purity 97%, 0.59 mol) in 500 ml of ethyl ether was dripped into the flask by means of a dropping funnel while keeping the reaction temperature in the range of 10° to 20° C., which dripping took about an hour. Then, while keeping the temperature of the mixture at about 10° C. the mixture was stirred for an hour.

Next, the reaction solution was poured into 500 ml of cooled and saturated ammonium chloride, and this solution was acidified with 5N hydrochloric acid. As the reaction solution separates into two layers, the lower organic layer was isolated, and ethyl ether was extracted from the upper water layer twice and the extracted ethyl ether was added to the isolated organic liquid. This organic liquid was washed with a saturated sodium hydrogencarbonate and then with saturated salt water, and was dried with magnesium sulfate.

Next, the solvent was removed by distillation, and the resulting reaction product was distilled under a reduced pressure, and a tertiary alcohol in an amount of 245 g (purity 97%, yield 79%) represented by the following formula was obtained as the fraction corresponding to the boiling point of 84°–85° C./32 mmHg.

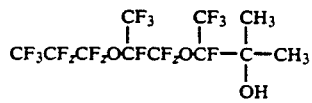

This tertiary alcohol was subjected to an elemental analysis and a GC-MS analysis, and the infrared absorption spectrum and $^1$H-NMR spectrum were taken. The result is as follows:

| elemental analysis | | | |
|---|---|---|---|
| | C | H | F |
| calculated values* (%) | 25.90 | 1.38 | 63.31 |
| actually measured values (%) | 25.58 | 1.41 | 63.02 |

*calculated values based on the assumption of $C_{11}F_{17}H_7O_3$
GC-MS: m/e 510 (M$^+$)

infrared absorption spectrum: Peaks were observed at 3640 cm$^{-1}$ and 3470 cm$^{-1}$ which are attributable to an OH group.

$^1$H-NMR spectrum: solvent: DMSO-d$_6$/CCl$_4$; internal standard: TMS; δ (ppm): 4.27 (s,1H,—OH); 2.70 (s,6H,2X CH$_3$)

Next, a flask having a content volume of 0.5 l was equipped with a simple distillation set, and poured into this flask were the above tertiary alcohol in an amount of 158 g (0.30 mol), 95% sulfuric acid in an amount of 200 g (1.94 mol), and, as the polymerization inhibitor, t-butylhydroquinone (TBHQ) in an amount of 0.25 g. The mixture was stirred for four hours at 150° C.; and at the same temperature an organic substance was distilled under a reduced pressure.

The organic layer of the distillate was washed with saturated sodium hydrogencarbonate and then with saturated salt water, and was dried with magnesium sulfate.

This organic layer was distilled, and an alkene in an amount of 128 g (yield 85%) was obtained, represented by the following formula, as the fraction corresponding to the boiling point of 147°–148° C.:

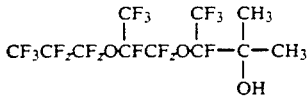

This alkene was subjected to an elemental analysis and a GC-MS analysis, and the infrared absorption spectrum and $^1$H-NMR spectrum were taken. The result is as follows:

| elemental analysis | | | |
|---|---|---|---|
| | C | H | F |
| calculated values* (%) | 26.85 | 1.02 | 65.63 |
| actually measured values (%) | 26.59 | 1.08 | 65.51 |

*calculated values based on the assumption of $C_{11}F_{17}H_5O_3$
GC-MS: m/e 492 (M$^+$), 473 (M-19) 492, M-19: 473 infrared absorption spectrum:

The peaks at 3640 cm$^{-1}$ and 3470 cm$^{-1}$ disappeared and a new peak was observed at 1660 cm$^{-1}$ which is attributable to a C=C group.

$^1$H-NMR spectrum: solvent: CCl$_4$; internal standard: TMS; δ (ppm): 5.30–5.70 (m,2H,=CH$^2$); 1.93 (s,3H,CH$_3$)

In an autoclave, 87.4 g (0.178 mol) of alkene, 35.0 g (0.25 mol) of trichlorosilane, and 1.50 g. (1.50×10$^{-4}$ mol) of n-butanol modified catalyst of chloroplatinic acid (Pt concentration 2.0 wt. %) were mixed together, and the reaction was allowed to proceed at 110° C. for 64 hours. Conversion ratio of GLC was 40%, and selectivity was 85%. After the reaction, the mixture was distilled under the atmospheric pressure, and the fraction corresponding to the boiling point of 145°–148° C. was obtained in an amount of 44.6 g (alkene, the starting material).

Next, the fraction was further distilled under a reduced pressure and the fraction corresponding to the boiling point of 86°–88° C./8 mmHg represented by the following formula (1a) was obtained in an amount of 40.4 g (yield 36%):

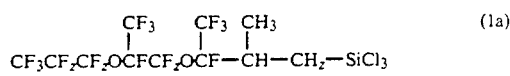 (1a)

This compound was subjected to an elemental analysis and a GC-MS analysis, and the infrared absorption spectrum and $^1$H-NMR spectrum were taken. The result is as follows:

| | C | H | Cl | F |
|---|---|---|---|---|
| calculated values* (%) | 21.05 | 0.96 | 16.95 | 51.46 |
| actually measured values (%) | 22.21 | 9.89 | 16.52 | 51.30 |

*calculated values based on the assumption of $C_{11}Cl_3F_{17}H_6O_2$ Si
GC-MS: m/e 627 (M$^+$)

IR spectrum:

FIG. 1 shows the spectrum chart, in which the peak at 1660 cm$^{-1}$ representing the C=C group disappeared.

$^1$H-NMR spectrum: solvent: CCl$_4$ internal standard: TMS; δ (ppm): 5.33 (m,1H,CH), 3.50 (m,2H,CH$_2$), 2.70 (m,3H,CH$_3$)

EXAMPLE 2

In a manner similar to Example 1, magnesium in an amount of 18 g (or 0.75 mol), methyl iodide in an amount of 115 g (0.75 mol), and ethyl ether in an amount of 150 ml were put together to prepare a solution of CH$_3$MgI. To this was dripped a solution obtained by adding 104 g (0.30 mol) of an ester, represented by the following formula, to 150 ml of ethyl ether, and the mixture was let to undergo a reaction at room temperature for two hours. Thereafter, the resulting product was treated and refined in the similar manner as in Example 1.

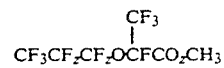

The reaction product was then distilled, and a tertiary alcohol, represented by the following formula, in an amount of 84 g (yield, 81%) was obtained as the fraction corresponding to the boiling point of 133°–135° C.:

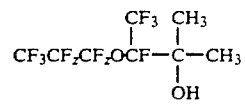

This tertiary alcohol was subjected to an elemental analysis and a GC-MS analysis, and the infrared absorption spectrum and $^1$H-NMR spectrum were taken. The result is as follows:

| | C | H | F |
|---|---|---|---|
| calculated values* (%) | 27.92 | 2.05 | 60.72 |

-continued

| | C | H | F |
|---|---|---|---|
| actually measured values (%) | 27.51 | 2.01 | 60.58 |

*calculated values based on the assumption of $C_8F_{11}H_7O_2$
GC-MS m/e 344 (M⁺)

infrared absorption spectrum:

Peaks were observed at 3650 cm$^{-1}$ and 3450 cm$^{-1}$ which are attributable to an OH group.

$^1$H-NMR spectrum: solvent: CCl$_4$ internal standard: TMS; δ (ppm) 2.47 (s,1H,—OH), 1.40 (s,6H,2 × CH$_3$) Next in the same apparatus used in Example 1, 82 g (0.24 mol) of the tertiary alcohol obtained in the above procedure, was added to 250 g (2.42 mol) of 95% sulfuric acid, and the mixture was strongly stirred for five hours at a temperature from 110° to 120° C. Then, in a similar manner to Example 1, the mixture was distilled, washed, and dried, and the resulting reaction product was further distilled to obtain 2-methyl-3-trifluoromethyl-4-oxa-3,5,5,6,6,7,7,7-octafluoropentene-1, represented by the following formula, in an amount of 73 g (yield 93%), as the fraction corresponding to a boiling point of 96° C.

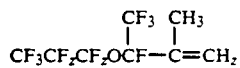

Similarly as in Example 1, this compound was subjected to an elemental analysis and a GC-MS analysis, and the infrared absorption spectrum and $^1$H-NMR spectrum were taken. The result is as follows:

| elemental analysis: | | | |
|---|---|---|---|
| | C | H | F |
| calculated values* (%) | 29.47 | 1.55 | 64.08 |
| actually measured values (%) | 29.31 | 1.58 | 64.00 |

*calculated values based on the assumption of $C_5F_{11}H_5O$
GC-MS: m/e 326 (M⁺)

infrared absorption spectrum:

The peaks at 3650 cm$^{-1}$ and 3450 cm$^{-1}$ attributable to an OH group disappeared and a new peak was observed at 1660 cm$^{-1}$ which is attributable to a C=C group.

$^1$H-NMR spectrum: solvent: CCl$_4$ internal standard: TMS; δ (ppm): 5.30–5.60 (m,2H,=CH$_2$), 1.90 (s,3H,CH$_3$)

In an autoclave, 65 g (0.20 mol) of the compound obtained above, 35 g (0.25 mol) of trichlorosilane, and 0.90 g (9.2×10$^5$ mol) of n-butanol modified catalyst of chloroplatinic acid (Pt concentration: 2.0 wt %) were mixed together, and a reaction was let to proceed at 110° C. for 64 hours. (Conversion ratio by GLC was 92%, and the selectivity was 98%). After the reaction, the mixture was distilled under atmospheric pressure, and the fraction corresponding to the boiling point of 93°–98° C. was obtained in an amount of 22.0 g (alkene, the starting material). Next, the fraction was further distilled under a reduced pressure and the fraction corresponding to the boiling point of 66°–67° C./10 mmHg represented by the following formula (1b) was obtained in an amount of 47.8 g (yield 50%):

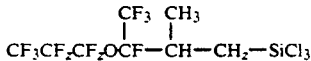

Thus obtained compound was subjected to an elemental analysis and a GC-MS analysis, and the infrared absorption spectrum and $^1$H-NMR spectrum were taken. The result is as follows:

| | C | H | Cl | F |
|---|---|---|---|---|
| calculated values* (%) | 20.82 | 1.31 | 23.04 | 45.28 |
| actually measured values (%) | 20.65 | 1.33 | 22.95 | 45.02 |

*calculated values based on the assumption of $C_8Cl_3F_{11}H_6O$ Si
GC-MS: m/e 461 (M⁺)

IR spectrum:

FIG. 2 shows the spectrum chart, in which the peak at 1660 cm$^{-1}$ representing the C=C group disappeared.

$^1$H-NMR spectrum: solvent: CCl$_4$; internal standard: TMS; δ (ppm): 5.66 (m,1H,CH=), 3.80 (m,2H,=CH$_2$), 2.83 (m,3H,CH$_3$)

EXAMPLE 3

A 46.0 g (0.094 mol) of the alkene obtained in a manner similar to Example 1, represented by the following formula, was mixed with 15 g (0.12 mol) of methyldichlorosilane and 0.80 g (9.2×10$^{-5}$ mol) of n-butanol modified catalyst of chloroplatinic acid (Pt concentration: 2.0 wt. %).

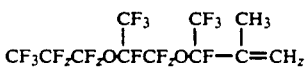

Then the mixture was allowed to undergo a reaction in the same manner as in Example 1 except that the reaction time was 96 hours. (Conversion ratio by GLC was 45%; selectivity was 68%.) After the completion of the reaction, the mixture was distilled under atmospheric pressure, and the fraction corresponding to the boiling point of 145°–148° C. was obtained in an amount of 25.8 g (alkene, the starting material). Next, the fraction was further distilled under a reduced pressure and the fraction corresponding to the boiling point of 85°–86° C./12 mmHg represented by the following formula (1c) was obtained in an amount of 16 5 g (yield 29%):

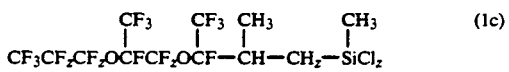

Thus obtained compound was subjected to an elemental analysis and a GC-MS analysis, and the infrared absorption spectrum and $^1$H-NMR spectrum were taken. The result is as follows:

| | C | H | Cl | F |
|---|---|---|---|---|
| calculated values* (%) | 23.74 | 1.49 | 11.68 | 53.19 |
| actually measured values (%) | 23.66 | 1.51 | 11.52 | 53.15 |

*calculated values based on the assumption of $C_{12}Cl_2F_{17}H_9O_2Si$
GC-MS: m/e 606 (M⁺)

IR spectrum:

FIG. 3 shows the spectrum chart, in which the peak at 1660 cm$^{-1}$ representing the C=C group disappeared.

$^1$H-NMR spectrum: solvent: CCl$_4$; internal standard: TMS: δ (ppm): 4.66 (m,1H,CH), 1.0–1.63 (m,5H,CH$_3$+CH$_2$), 0.83 (s,3H,SiCH$_3$)
What is claimed as new and desired to be secured by Letters Patent of the United States is:
1. Fluorine-containing organic silicon compounds represented by the following general formula:
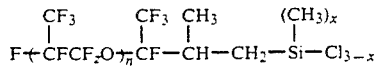
wherein n is any integer of 1 to 4, and x is any integer of 0 to 3.
* * * * *